US00PP10747P

United States Patent [19]

Osiecki

[11] Patent Number: Plant 10,747

[45] Date of Patent: Jan. 5, 1999

[54] ANTHURIUM PLANT 'A7'

[75] Inventor: Marian W. Osiecki, Marianna, Fla.

[73] Assignee: Oglesby Plants International, Inc., Altha, Fla.

[21] Appl. No.: 859,474

[22] Filed: May 19, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 8,540 1/1994 Rotolante ..... Plt./88.1

P.P. 9,355 10/1995 Henny ..... Plt./88.1

*Primary Examiner*—Howard J. Locker
*Assistant Examiner*—Kent L. Bell
*Attorney, Agent, or Firm*—Rothwell, Figg, Ernst & Kurz

[57] ABSTRACT

A new and distinct cultivar of Anthurium is provided. It is a medium to large size plant, suitable for production in 15 cm to 25 cm pots from a single tissue culture produced microcutting with vigorous growth, early and year-round flowering. Striking, large, red, glossy spathes are carried on thick, strong, distally red-brown peduncles mostly above foliage and sharply contrast with dark green, glossy, large, thick leaves.

2 Drawing Sheets

SUMMARY OF THE INVENTION

This invention relates to a new and distinct Anthurium cultivar characterized by the following combination of repeatedly observed traits:

1. Medium to large size plant,
2. vigorous growth,
3. large, thick, leathery, dark green and glossy leaves,
4. early and year-round flowering,
5. prominent, large, red, glossy spathes with greyed-purple spadixes,
6. spathes held mostly above foliage on thick, strong, distally red-brown peduncles, and primarily selected for those characteristics being so selected from the progeny of the cross stated below being grown near Altha, Fla. in a cultivated area.

ORIGIN AND ASEXUAL REPRODUCTION

Asexual reproduction of this cultivar by tissue culture was directed by me, such reproduction establishing that the plant does in fact maintain the characteristics described in successive generations. The plant was initially selected where grown in a planned breeding program in or near Altha, Fla. and has been reproduced by tissue culture in the vicinity of Altha, Fla. since 1993 with the characteristics stated. The female parent was a selected clone of Anthurium 'Ruth Morat' U.S. Plant Pat. No. 8,450, a/k/a Lady Ruth™ and the male parent was a selected seedling of *Anthurium andreanum* with large red spaths designated AR 891 patent no applied for. The cross was made in 1991 and the seedling was selected in 1992. This new cultivar has been identified as Anthurium 'A7'. It is possible that other identification will be adopted in the trade, but the name selected will serve for the purposes hereof.

BRIEF DESCRIPTION OF THE PHOTOGRAPHS

The accompany photographs show as nearly true as it is reasonably possible, in a color illustration of this character, typical specimens of the plant parts of the new cultivar. The plant of 'A7' was approximately 16 months from planting a single tissue culture produced microcutting and was grown in a 15 cm pot.

In the photographs:

DETAILED DESCRIPTION OF THE NEW CULTIVAR

Figure 1:
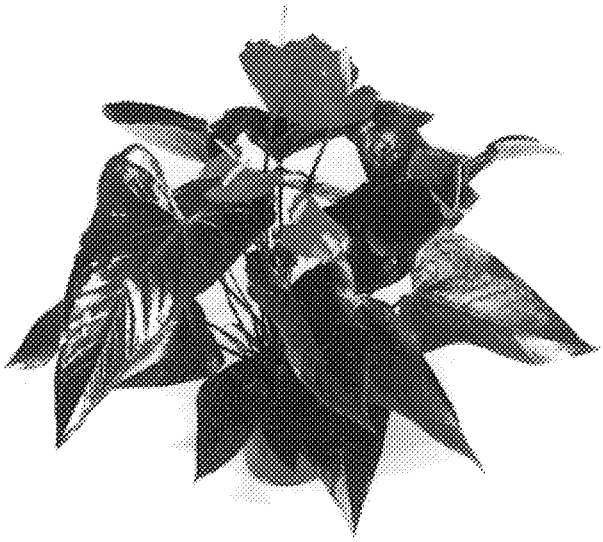
FIG. 1 depicts the whole plant.
Figure 2:
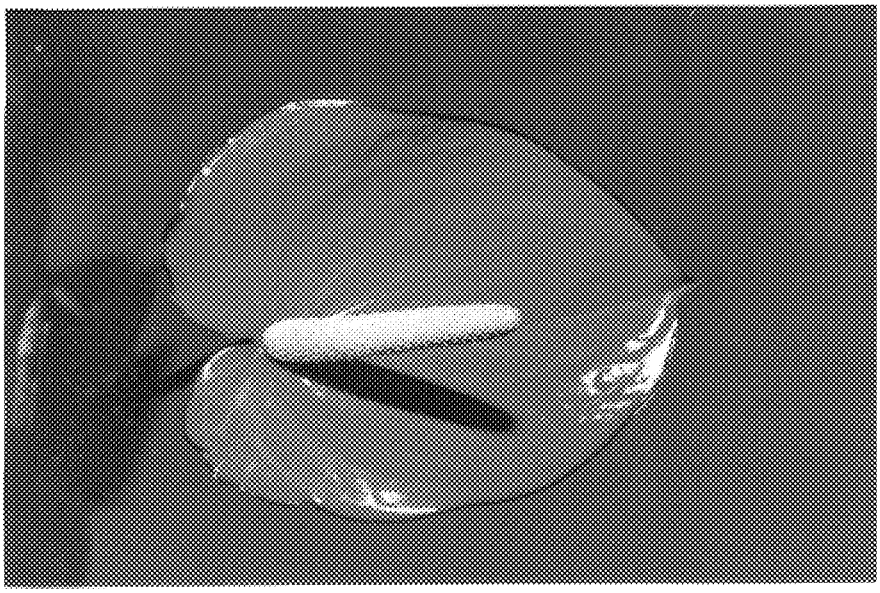
FIG. 2 illustrates the mature inflorescence.
Figure 3:
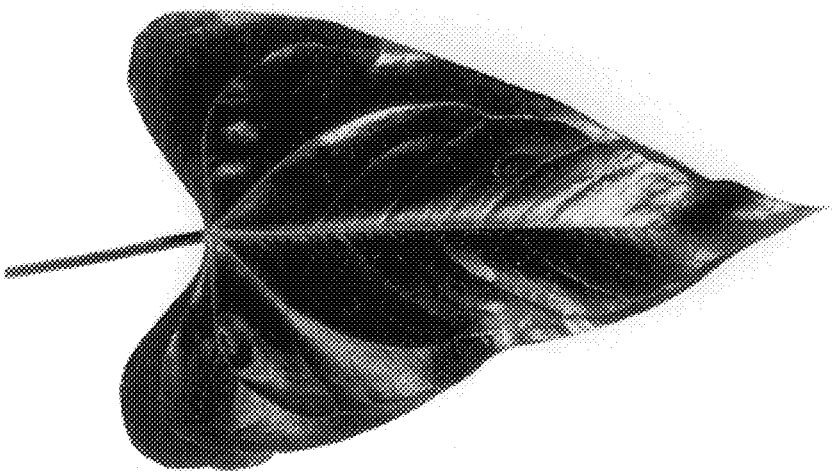
FIG. 3 illustrates the top of a mature leaf.
Figure 4:
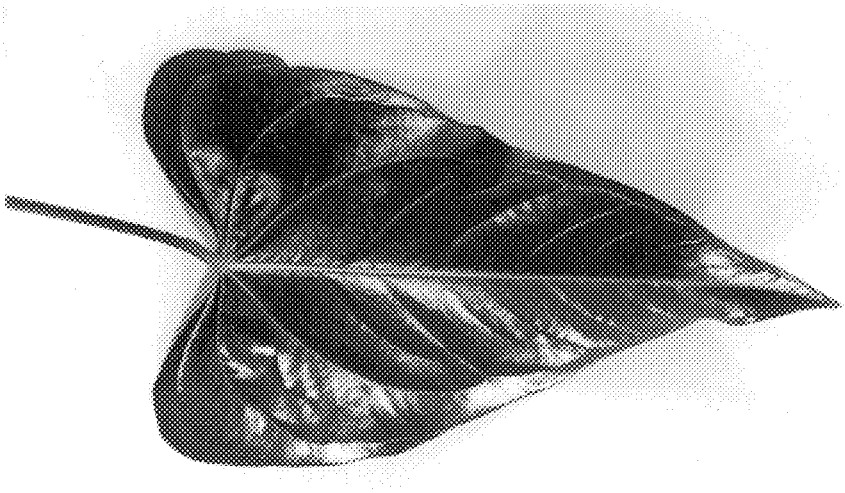
FIG. 4 illustrates the bottom of a mature leaf.

The following observations and measurements describe plants grown near Altha, Fla. under greenhouse conditions. These observations and measurements were recorded in January and February 1997 from mature plants (about 15 months from planting tissue culture produced microcuttings) grown in 15 cm pots. Youngest fully developed organs on a main stem were used for measurements and color description, unless otherwise indicated. Color values were determined under natural, indirect light of approximately 600–850 foot-candles. Color references are made to the RHS... Colour Chart, except where general color terms fo ordinary significance are used. 'A7' has not been observed under all possible environmental conditions. The phenotype may vary with variations in environment and horticultural practices, such as, temperature, light intensity, day length, fertilization, propagation procedure etc., without any change in genotype.

Botanical classification: Anthurium hybrid cultivar 'A7'.

Parentage:

*Female parent.*—Selected clone of Anthurium 'Ruth Morat' U.S. Plant Pat. No. 8,540.

*Male parent.*—Selected seedling of Anthurium andreanum with large red spathes designated 'AR 891'not patented.

Propagation: Plant tissue culture.

Plant descriptions:

*Growth habit.*—Medium to large size, relatively open.

*Height.*—Foliage 39–51 cm; with spathes 51–61.5 cm.

*Maxium width.*—67–88 cm.

Petiole:

*Size.*—28.0–39.0 cm long, 5.3–6.3 mm in diameter below geniculum.

*Geniculum.*—3.2–4.0 cm long, 6.2–7.5 mm in diameter at the base; sometimes petiole slightly bends at the base of geniculum.

*Petiole wings.*—5.0–9.2 cm long.

*Color.*—Geniculum: Adaxial: Colors resembling 166A, 165A, 176A, 177A (all greyed-orange), 178A (greyed-red) and 183A-B (greyed-purple) along the shallow, longitudinal, central groove gradually merge with 146A-B (yellow-green) on the sides. Abaxial: 144A(yellow-green). Below Geniculum: Adaxial: Similar to 200C-D (brown) and 165A (greyed-orange) with green spots; the amount of green increases proximally. Abaxial: Very short zone immediately below geniculum similar to 146B and 144A (both yellow-green) proximally merges with color resembling 152A (yellow-green) and 199A (greyed-brown); midlength area slightly resembles 200D (brown); the base is yellow-green (146A or 144A). Green lenticels are visible on brownish portion of petiole. Petiole wings: 146A-B (yellow-green) with brown-red edge. Petioles of young leaves have more orange, red, purple and brown colors than those of mature leaves.

Leaf blade:

*Shape.*—Ovate; tip acuminate with aristate tendencies, sometimes slightly asymmetric; base truncate, often slightly asymmetric. Leaves produced at very early stage of plant development have more truncate bases. Lobes usually slightly curve upwards.

*Size.*—31.5–37.0 cm long, 20.2–23.0 cm wide; length to width ratio 1.5–1.8:1.

*Texture.*—Thick, leathery, smooth, glossy; young leaves highly polished.

*Veins.*—Prominent near the base, less conspicuous near the tip.

*Color.*—Newly unrolled leaf: Adaxial: Similar to, but usually more green than 146A (yellow-green). Veins in proximal area 146B-C, 144A (both yellow-green) with some greyed-red-purple tint on short portions near the base. Distally veins approximate the color of surrounding tissue. Abaxial: 146B. Edge red-purple. Mature leaf: Adaxial: Darker than 147A (yellow-green). Veins: Most of midrib and proximal portions of primary veins similar to 146A-B (yellow-green); greyed-red-purple coloration near base gradually disappears. Distal portions of veins approximate the color of surrounding tissue. Abaxial: Similar to, but a little more green than 146A.

Scale leaves:

*Covering lateral bud penultimate to the mature inflorescence.*—Length: 12.6–16.4 cm. Color: Abaxial: Proximal central zone darker than 144A (yellow-green), except 144B-C at base; lateral zones 144B-D. In the distal approximately ¾ the colors: 144A and darker and 146A-B occur. Edges in the distal half have some red tint. Adaxial: Proximal zone white with green (139D) edges. Distally, greyed-red colors (180 A-B, 178A-B, 181A-B, 179A) accur in increasing amounts. Tip is mostly greyed-red.

*Between peduncle of young inflorescence and stem.*—Length: 5.0-14 6.0 cm. Color: (Abaxial): Yellow-green with greyed-red edges in distal half; two longitudinal elevated ribs each have a dotted brown line.

Inflorescence:

*Arrangement.*—Mature spathes situated mostly above foliage, approximately horizontal with spadix leaning backward. Spadix low on the spathe. Ratio spathe length to spadix length 1.9–2.1:1.

Peduncle:

*Size.*—46.3–53.0 cm long, 6.07–7.3 mm in diameter immediately below spathe.

*Stipe.*—Very short (not measurable).

*Color.*—Front: Colors resembling 174A, 175A-B, 177B, 176A-B, 173A (greyed-orange) variably occur in distal half. The proximal half becomes more brown and eventually more green near base. Back: Approximately 2 cm zone below spathe similar to 178A-B (greyed-red) except some 45A-B (red) adjacent to spathe. Peduncles tend to become less red whey they mature. Proximally the colors: 173A, 175A-C, 178C variably occur. Proximal half has more brown color than the distal half. Base surrounded by petile wings is predominantly green. Old peduncles usually become predominantly green.

Spathe:

*Shape.*—Ovate, often asymmetric, sometimes slightly cupped through senescence; tip aristate with edges rolling frontwards; base cordate, often asymmetric with wavy margin; lobes extend 2.0–2.9 cm past peduncle.

*Size.*—13.0–15.3 cm long, 9.7–11.6 cm wide; length to width ratio 1.3–1.5:1.

*Texture.*—Smooth, leathery, highly polished.

*Color.*—Closed bud: Varies between 46A and 53B (both red) near base; distally becomes darker merging with 53A near tip. Newly unrolled spathe: Front: 53A or a little darker near base; distally much darker. Back: 53A or a little lighter near base; darker than 53A near tip. Near spadix and along midrib in proximal half a little lighter than 46A. Margin on both sides marked by a narrow greyed-purple band (similar to 187A-B) that tapers and becomes lighter near base. Mature spathe: Front: Similar to 53A. generally the area near spadix is the lightest and the area near tip the darkest. Back: 53B near base gradually becomes darker than 53A near tip, except for the areas near spadix and along midrib (especially in the proximal half), which are similar to 45B (red). Margin similar to that of a newly unrolled spathe. Spathe retains red color for approximately two months following appearance of bud above or among leaves and then gradually turns green.

Spadix:

*Size.*—6.7–7.5 cm long; 9.2–10.4 mm maximum diameter.

*Flower density.*—Approximately 14–16 flowers in a straight longitudinal line on a 2-cm long middle portion of the spadix.

*Color.*—Color of spadix is determined by the perianth color. Young influorescence (with newly unrolled spathe and first protruding pistils): Similar to 186A-B (greyed-purple) in proximal half gradually merging with 48A (red) in distal zone. Mature inflorescence (with pistils visible on more than ¾ of spadix): Proximal zone with pistils similar to 186C with some gradation from lighter to darker in the distal direction. A few mm zone near tip similar to 186A-B; tip 51A-B (red).

Botanical flower:

*Perianth.*—Prominent between small pistils, segments united. Perianth of an individual flower appears on the spadix surface as almost a diamond shape, approximately 3.0–3.5 mm long and 2.0–2.5 mm wide.

*Pistil.*—Approximately 2 mm long, 1 mm wide; protrudes fraction of a mm beyond perianth, white, translucent. Stigma minute.

*Stamen.*—Approximately 1.2–1.5 mm long, 0.8–1.0 mm wide, white, translucent, not visible at the flower maturity. Only top of the anther protrudes slightly beyond perianth at the time of pollen release.

*Pollen.*—Scarce amount of white pollen sometimes produced. Spontaneous seed production very rare.

Flowering: Flowers naturally in 12.5 cm pots, about 9–11 months from planting tissue culture produced microcuttings. Continuous year-round flowering. At approximately 15 months four to seven spathes are visible above and among leaves.

Roots:

*Roots above soil level.*—Few, short, low on the stem, thick, fleshy, non-branching; young aerial roots red (53A) or greyed-purple (185A), root cap dark yellow. Old aerial roots gray.

*Roots below soil level.*—Very strong root system; numerous primary roots, thick, fleshy. Young primary roots red (47A-B) or greyed-red (179A-B, 180A-B) with yellow root caps. Secondary roots lighter in color to almost white.

Disease and Insect resistance: No unusual susceptibility to diseases or insects noted to date.

Comparison with the Known Cultivars:

The new cultivar can be compared to the known cultivars 'Ruth Morat' U. S. Plant Pat. No. 8,540 a/k/a 'Lady Ruth'™ and to '75-10' U. S. Plant Pat. No. 9,355 a/k/a 'Red Hot'™. The comparisons were made on plants grown under smilar conditions in a greenhouse near Altha, Fla.

'A7' is distinguished from both cultivars by its larger size; more open growth habit; less branching; more vigorous growth; earlier flowering; larger leaves; larger inflorescences; brighter red, more glossy spathes.

'A7' is further distinguished from 'Ruth Morat' by higher position of spathes in relation to foliage; darker petioles and peduncles and by cordate leaf blade bases.

'A7' is further distinguished from '75-10' by lower position of spathes in relation to foliage and by lighter colored peduncles.

I claim:

1. A new and distinct cultivar of Anthurium plant named 'A7', substantially as described and illustrated herein, characterized particularly as to novelty by its medium to large size; relatively open growth habit; vigorous growth; large, thick, dark, glossy leaves; early, year-round flowering; large, red, glossy, long-lasting spathes carried on thick, strong, distally red-brown peduncles mostly above foliage and by greyed-purple spadixes.

* * * * *